United States Patent [19]

Ciotti

[11] Patent Number: 5,356,815
[45] Date of Patent: Oct. 18, 1994

[54] APPARATUS FOR MICROBIOLOGICAL ANALYSIS OF BIOLOGICAL SAMPLES IN LIQUID SUSPENSION BY LIGHT-SCATTERING TECHNIQUE

[75] Inventor: Alfredo Ciotti, Udine, Italy

[73] Assignee: S.I.R.E. Sas di De Monte R., Italy

[21] Appl. No.: 43,746

[22] Filed: Apr. 7, 1993

[30] Foreign Application Priority Data

Apr. 16, 1992 [IT] Italy .................... UD92A000061

[51] Int. Cl.$^5$ .................................................. C12M 1/34
[52] U.S. Cl. ............................ 435/291; 435/284; 435/296; 435/300; 435/808; 436/164; 436/165
[58] Field of Search ................ 356/343, 338; 436/164, 436/165; 435/808, 296, 291, 300, 284

[56] References Cited

U.S. PATENT DOCUMENTS 5,084,629 1/1992 Petralli ........................... 356/343
5,104,221 4/1992 Bott et al. ....................... 356/343
5,155,543 10/1992 Hirako ........................... 356/343

*Primary Examiner*—Donald E. Czaja
*Assistant Examiner*—Lien Tran
*Attorney, Agent, or Firm*—Nixon & Vanderhye

[57] ABSTRACT

An apparatus for microbiological analysis of biological samples in liquid suspension by light-scattering technique, which employs test-tube containers (11) made of a material transparent to electromagnetic radiations of a determined wave length. Each container (11) cooperating with a thermostat system (17) and at least momentarily with a stirring assembly (31) and relative keeper stirring means (18). The container (11) cooperating with a focussing and collimation system (22) and with a monitoring device (24), is illuminated by electromagnetic radiation of a determined wave length (74) emitted with its own axis (29) of emission and transmitted through the container (11) by the focussing and collimation system (22). The radiation is scattered by any microorganisms present in the sample with an intensity related to their number and morphology. This scattered radiation is picked-up in succession with desired timing by the monitoring device (24) according to determined angles, from 0° to 180°, in relation to the emission axis (29). A computer collects the resulting data and constructs a curve representing intensity of scattered radiation versus time. The curve parameters are compared with reference values contained in a data bank of the computer (13) for determination of the typical parameters of the analysis i.e., the counting, the replication rate and the morphology of microorganisms present in the sample.

10 Claims, 2 Drawing Sheets

APPARATUS FOR MICROBIOLOGICAL ANALYSIS OF BIOLOGICAL SAMPLES IN LIQUID SUSPENSION BY LIGHT-SCATTERING TECHNIQUE

BACKGROUND OF THE INVENTION

1. Field of the Invention

This invention concerns a method and apparatus for microbiological analysis of biological samples in liquid suspension by light-scattering technique, as set forth in the respective main claims.

To be more exact, the invention concerns a method and apparatus for monitoring the quantity and quality of colonies of microorganisms present in the samples.

The method according to the invention and the relative apparatus find their proper application in analysis laboratories which perform advantageously, but not only, the microbiological analysis of urine, blood, faeces, etc.

2. Discussion of Prior Art

According to the state of the art the analysis of biological samples such as urine, blood, etc. can be carried out substantially according to two methods depending on the information to be obtained.

In particular, chemical-clinical analysis provides information about the chemical composition of the biological sample and identifies the percentages and concentration of the various chemical elements contained in the sample, whereas microbiological analysis has the purpose of identifying the presence of bacteria, which are important from a pathological point of view, and then of establishing the type and concentration of those bacteria. As regards this latter case various techniques are known at present for the evaluation of the presence/absence, number and species of bacteria contained in those biological samples.

The technique accepted everywhere and most used is based on so-called urinoculture, which consists in the distribution of known volumes of possibly diluted biological samples on plates known as Petri dishes and containing culture media suitable for replication of any bacterial colonies in the samples.

Quantitative evaluation of the bacteria in the culture after a given period of time enables information to be obtained about the initial concentration of these bacteria in relation to the volume of the sample used and the dilution factor employed.

The length of the time required to obtain results in a form which can be evaluated is seldom less than 18 hours and in most cases is about 24 hours.

Moreover, the calculation is based on visual evaluations of the final bacterial distribution and on considerations of a statistical type applied by the operator of the apparatus and therefore does not ensure absolute accuracy of the method.

Furthermore, this method, as it does not have available initial information about the presence/absence of the bacteria, entails a heavy work load and a superabundance of equipment in the event of a great percentage of negative cultures to be evaluated.

Methods are known which make use of the occurrence of special chemical reactions of the biological samples when subjected to given treatments.

These methods give speedy information about the presence/absence of bacteria and thus enable the positive samples to be separated from the negative samples in a short time.

But so as to evaluate the concentration and type of the bacteria in the positive cases thus selected it is always necessary to make use of the method of bacterial culture detailed above.

Moreover, these chemical methods may be upset by aspecific reactions which affect the reliability of the results achieved.

Combined methods of a biochemical type exist which are based on evaluation of the variations of absorbed radiation and colour changes in various media on which the sample being examined is distributed References to these methods are considered in patents Nos. EP-A-0301699, U.S. Pat. No. A-3,322,956, U.S. Pat. No. A-4,577,970, FR-A-2.350.393.

These latter methods yield qualitative information about the species present in relatively short times of the order of 5 to 12 hours, but the results may not be accurate .

Furthermore, these methods do not provide quantitative type of information and, thus, do not allow to define the curve of replication of microorganisms.

Furthermore, the cost of this evaluation method is especially high, and also the problem remains of having to carry out the whole analysis step also on samples which are then found to be negative.

Next, the traditional methods do not provide information concerning the presence in the sample of corpuscular components such as leukocytes, erythrocytes and salts, and this information has to be obtained by specific analyses of a type different from the types described above.

SUMMARY OF THE INVENTION

The present applicants have studied, tested and obtained this invention so as to overcome the shortcomings of the state of the art and to achieve further advantages.

This invention is set forth and characterized in the main claims, while the dependent claims describe variants of the idea of the main solution.

One purpose of this invention is to provide a method and apparatus for the microbiological analysis of biological samples, the method and apparatus being able to give reliable and accurate results with a considerable saving of time and of equipment as compared to the methods of the state of the art while still maintaining the same philosophy as the classical reference model.

Another purpose of the invention is to provide a method which is displayed with a fully automated apparatus, which requires a very small working staff owing to automation of the reading steps, data processing, display of the results, etc.

A further purpose of the invention is to provide a method and apparatus capable of very great sensitiveness in establishing quickly the presence/absence of bacterial colonies in the biological sample.

Yet another purpose of the invention is to yield additional information about the presence, in a sample of urine for instance, of corpuscular components such as leukocytes, erythrocytes, salts, etc.

Another purpose of the invention is to enable samples to be introduced, even when the working cycle has been already started, if such samples are deemed worthy of priority over those already being analysed, for reasons of urgency, for instance.

A further purpose of this invention is to obtain data concerning the number, the growth rate and the morphology of microorganisms present in the sample.

The method according to the invention and the relative apparatus employ a light-scattering technique to obtain the correlation between the intensity of the scattered radiation and the number and morphology of microorganisms.

So as to carry out this technique, the invention arranges to insert a container holding the biological sample in an appropriate seating in a stand.

According to a variant a plurality of containers, each with its own biological sample, is included so as to speed up the cycle.

The biological samples are inoculated into an aqueous based solution of media favourable for the growth of the bacterial colonies initially present in the samples.

The containers are advantageously sterile test-tubes; all of them have substantially homogeneous sizes and thicknesses and are made of a material transparent to electromagnetic radiations of determined wave lengths, such as optical glass or a transparent plastic, for instance.

A data processing unit equipped with suitable peripherals such as a display, keyboard, printer, etc. cooperates with the stand and starts up and manages the whole analysis working cycle automatically.

A thermostat system operated by the data processing unit is included within the stand to keep the temperature of the samples controlled and constant.

Each test-tube contains a ferromagnetic metallic keeper, which is rested initially on the bottom of the test-tube. This metallic keeper cooperates with a stirring assembly provided with magnets; this stirring assembly, when started up by the data processing unit at the beginning of the cycle, rotates the metallic keeper in the test-tube, thus causing homogenization of the suspension.

This homogenization of the suspension of the growing bacteria is very useful to equalize the microorganisms growth independently of flotations, sedimentations and aggregations which are typical of the various bacterial species.

In the event of multiple test-tubes the apparatus according to the invention is equipped with a movable assembly, which enables the test-tubes to cooperate, one at a time, at pre-set intervals for pre-set times with a reading means, which is provided with a focussing and collimation system, advantageously consisting of optical lenses assemblies, prisms and/or mirrors, and with monitoring devices advantageously consisting of optoelectronic semiconductor devices, photo-resistors, light sensitive vacuum tubes.

The focussing and collimation system is associated with a means which generates electromagnetic radiation consisting of light sources, polarized or not, as filament lamp, semiconductor light emitter, laser device (semiconductor, gas or crystal type).

According to a first lay-out the test-tubes remain stationary and the reading means can move. In this case, when the reading means has been positioned in relation to the test-tube with the sample, the stirring assembly arranges to rotate the ferromagnetic metallic keeper and therefore to homogenise the suspension. The stirring assembly is one alone and is positioned by the movable assembly.

According to another lay-out each test-tube is associated with its own stirring assembly.

Thereafter the generator of electromagnetic radiation sends its radiation to the focussing and collimation system, which the reading means aligns with the test-tube.

At the end of the sample monitoring, the movable assembly brings the reading means into cooperation with the next test-tube.

According to a variant the reading means is stationary, whereas the stand with the test-tubes can be rotated to enable each test-tube to cooperate, one at a time, with the reading means at pre-set intervals.

The electromagnetic radiation can be polarised or not; this radiation emitted by the focussing and collimation system is scattered by the sample and picked up by the monitoring device.

The monitoring device comprises a plurality of monitors situated at different angles to the optical axis of the focussing and collimation system.

The monitors, can be of a discrete type positioned at determined angles or of a continuous type able to cover continuously the whole angle.

The monitors are arranged advantageously to cover substantially an angle which may vary between 0° and 180° in relation to the optical axis, since for reasons of symmetry the information obtained with monitors positioned to cover such angles provides the information needed for analysis of the sample being examined. p The scattered radiations picked up by the monitors are converted into electric signals and therefore sent to the data processing unit for processing and computing of the results.

The computation procedure is based on the fact that the bacterial growth within the suspension generates the variations of the light-scattering intensity with time.

Periodical readings of scattered radiation enable the construction, by means of known interpolation procedures, of the growth curve of the bacterial colonies within the sample being examined, this curve being related to the angle of monitoring at which the monitor is positioned.

It has been shown by experiments that the bacteria growth curve has a typical development as a function of time and may be described by the formula $C_B = Ae^K n(t-t_o) + C$.

In this formula $C_B$ is the intensity of the scattered radiation, A and C are constants which depend respectively on the bacterial species being examined and on the initial concentration, $K_n$ is a parameter which takes into account the angle of the positioning of the monitor, t is the time and $t_o$ is a delay-time related to the number of bacteria present in the sample.

By correlating this growth curve or, to be more exact, by correlating the characteristic parameters of formula $C_B = Ae^K n(t-t_o) + C$, such as A, C, $K_n$, etc. with standard values obtained experimentally and stored in a data bank in the data processing unit it is possible to obtain information useful for counting and identification of the bacteria in the sample.

The data bank can be built up by using one of the two following procedures, for instance.

The first procedure arranges to acquire samples of an already identified bacterial species, to introduce these samples into the apparatus according to the invention and to construct a characteristic curve related to that particular bacterial species.

The second procedure consists in using a sample with a bacterial species to be identified and, after separating it into two halves, for instance, in analysing the first half with the traditional method, Petri dishes for instance, and the second half with the method according to the invention.

In this way it is possible to associate with each bacterial species identified by means of the traditional method a particular growth curve obtained with the method according to the invention.

The data bank is built up by using a great number of these procedures, for instance of the order of hundreds for each characteristic monitoring angle.

In this way, for each bacterial species it is possible to evaluate the parameters of formula $C_B = Ae^K n(t-t_o) + C$, i.e. A, C, $K_n$, etc.

During analysis of the sample being examined the data processing unit calculates the parameters (formula $C_B = Ae^K n(t-t_o) + C$) of the growth curve obtained and compares them with the parameters stored in the the data bank and related to the various bacterial species.

By means of this comparison the data processing unit provides with a good level of reliability the identification of the bacterial species in the sample.

As the characteristic of the growth curve depends strictly on the monitoring angle, the monitoring angles must be the same as those used to build up the data bank.

With respect to the use of a single monitor located at a determined angle, the application of several monitors at different angles enables greater information to be obtained regarding the anisotropy of the signal, which is closely linked to the morphology of the microorganisms in suspension.

Referring to formula $C_B = Ae^K n(t-t_o) + C$, the parameters $C_B$ and $t_o$ are dependent on the number of bacteria present in the sample.

The number of bacteria, through $t_o$, conditions the evolution of the growth curve, that is obtained from the elaboration of the intensity of the scattered radiation.

From a practical point of view, the growth curve of a liquid suspension of bacteria corresponding to 50 millions CFU/ml may be recorded in less than one hour, the growth curve of a liquid suspension of bacteria corresponding to 30.000 CFU/ml may be detected and recorded in about three hours and the growth curve of a liquid suspension of bacteria corresponding to 5.000 CFU/ml in about five hours.

CFU/ml represents the unit of measurement recognized internationally and used for the bacterial population; CFU means "colony forming units".

The whole calculation procedure is automated and, when the cycle has been started, the data processing unit will provide as output, after the necessary time and by means of a display or printer, all the required information such as the initial bacterial concentration, speed of growth, presence of leukocytes or not, type of bacterium, etc.

BRIEF DESCRIPTION OF THE DRAWINGS

The attached figures are given as a non-restrictive example and show a preferred lay-out of the invention as follows.

DETAILED DISCUSSION OF PREFERRED EMBODIMENTS

Figure 1:
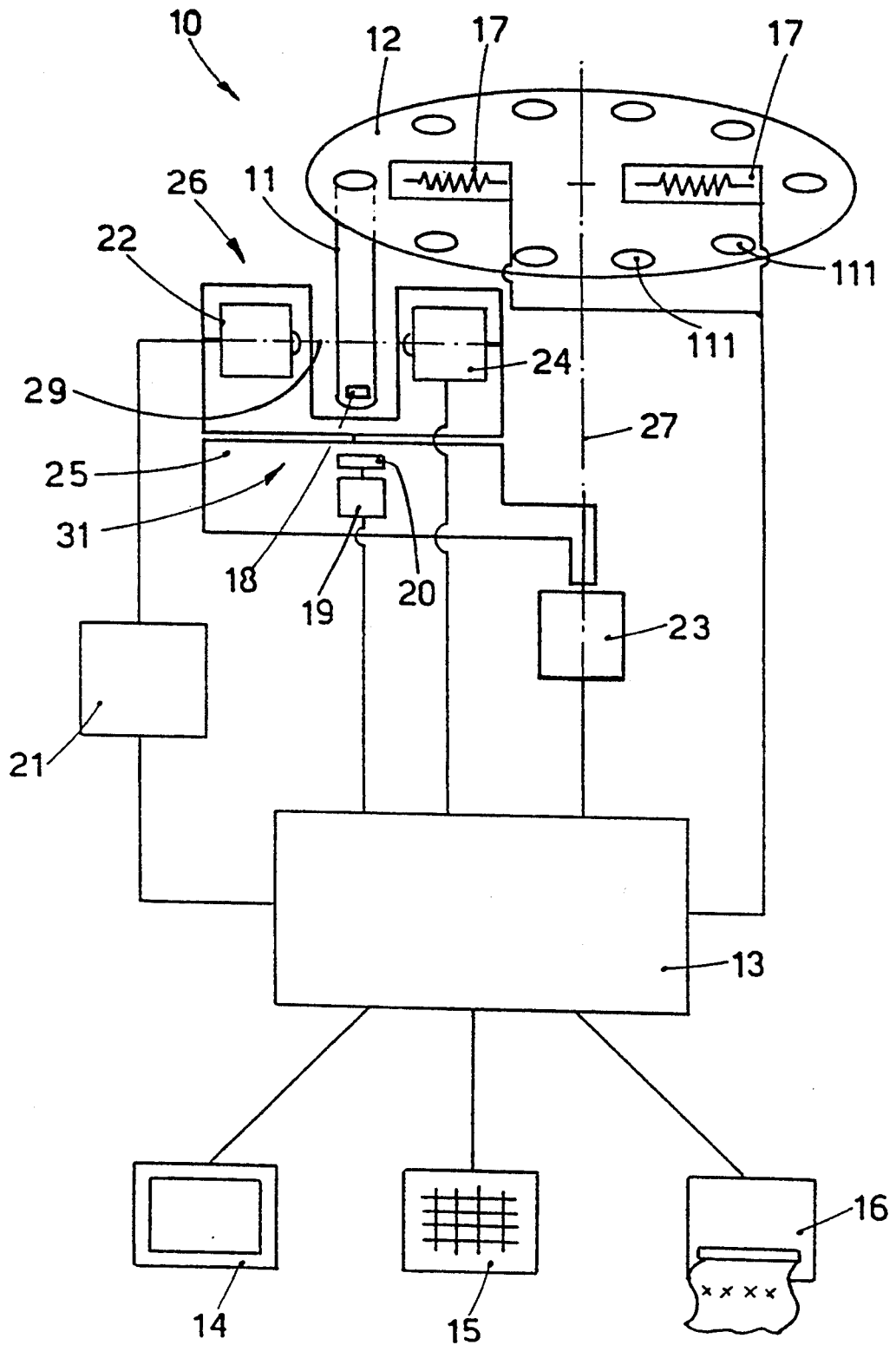
FIG. 1 shows with a block diagram the monitoring apparatus for microbiological analysis according to the invention.

The reference number 10 in FIG. 1 indicates an apparatus for the microbiological analysis of biological samples in liquid suspension by light-scattering technique.

The biological samples to be analysed are inoculated in suitable sterile containers 11 of a test-tube type with a vertical axis and homogeneous dimensions and thickness; the containers 11 are made of material transparent to electromagnetic radiations, such as glass, a plastic or another suitable material.

The containers 11 are advantageously hermetically sealed to prevent possible pollution by the surrounding environment.

The containers 11 are placed in appropriate seatings 111 in a stand 12; in this example the seatings 111 are arranged substantially along a circumference.

The stand 12 is connected to a data processing unit 13, which starts up and controls all the steps in the operating cycle of the analysis.

The data processing unit 13 governs all the peripherals needed for conversing with a user; in this case the peripherals are a display 14, keyboard 15 and printer 16.

The stand 12 contains thermostat means 17 governed by the data processing unit 13 to keep the temperature of the samples being analysed under control.

Each container 11 is equipped with a metallic keeper 18, which is rested initially on the bottom of the containers 11.

When the operating cycle is started, the data processing unit 13 sets in motion the stirring assembly 31, which in this case consists of a first motor 29 and magnets 20, which by setting in movement the keeper 18 within the container 11 now being examined enable the solution to be homogenised, thus avoiding problems due to sedimentations and aggregations typical of the growth of bacterial species.

According to the requirements the data processing unit 13 actuates a generator 21 of electromagnetic radiation, and the generator 21 sends a light beam to a focussing and collimation system 22.

The focussing and collimation system 22 cooperates with a monitoring device 24, and the system 22 and the device 24 together constitute a reading means 26.

The electromagnetic radiation generator 21 consists in this case of a laser emitter of polarized light working in a field of wave lengths ranging from 200 to 1000 nm.

The reading means 26 cooperates with a movable supporting and orienting assembly 25 for its alignment with the container 11 holding the sample being examined.

In this example the movable assembly 25 can rotate about a generating axis 27 of the circumference on which the seatings 111 are positioned.

The movable assembly 25 in this case is set in rotation by a second motor 23.

The movable assembly 25 supports and positions the monitoring device 24, which includes at least two monitors 28 located at different angles "$\alpha$" and "$\beta$" to an axis 29 of emission of the focussing and collimation system 22; these angles are pre-set and remain unchanged during the whole period of the analysis.

Figure 2:
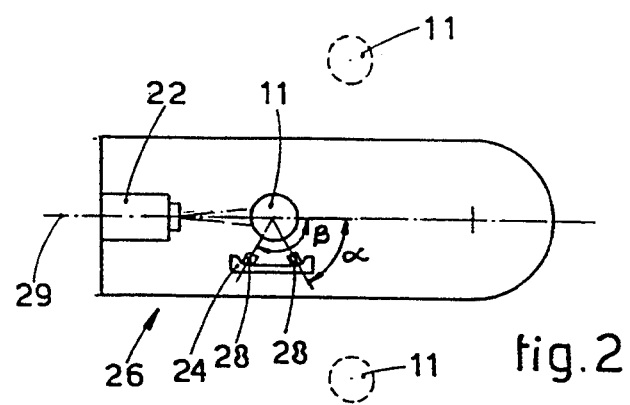
FIG. 2 shows a plan view of a possible embodiment of the reading means according to the invention.

In the example shown in FIG. 2 the monitoring device 24 consists of two monitors 28. This lay-out makes possible the monitoring of the light-scattering radiation, which may be caused by the presence of corpuscles within the container 11.

The angles are positioned advantageously on a plane orthogonal to the axis of the container 11.

At the end of the monitoring cycle, the second motor 23, by means of assembly 25, brings the reading means 26 and the stirring assembly 31 into cooperation with the next container 11.

According to a variant each container 11 is associated with its own stirring assembly 31.

According to a further variant the reading means 26 is stationary, whereas the stand ]2 can rotate and on each occasion brings a container 11 into cooperation with the reading means 26.

The radiations detected are converted into electrical signals by the monitors 28 and are sent to the data processing unit 13, which processes the data and calculates the results.

The monitoring cycle is repeated many times at regular intervals on each container ]1, thus enabling the data processing unit 13 to build lap for each sample a growth curve for the bacterial population in the sample through the interpolation of the discrete values tabulated as a function of time.

Figure 3A:
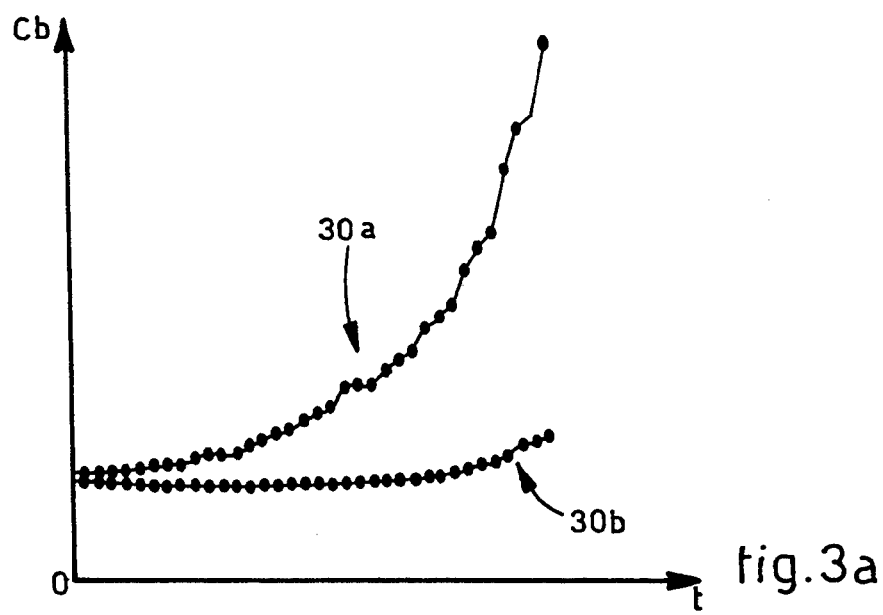
FIGS. 3a and 3b show examples of growth curves obtained by the method according to the invention for some particular bacterial species.
Figure 3B:
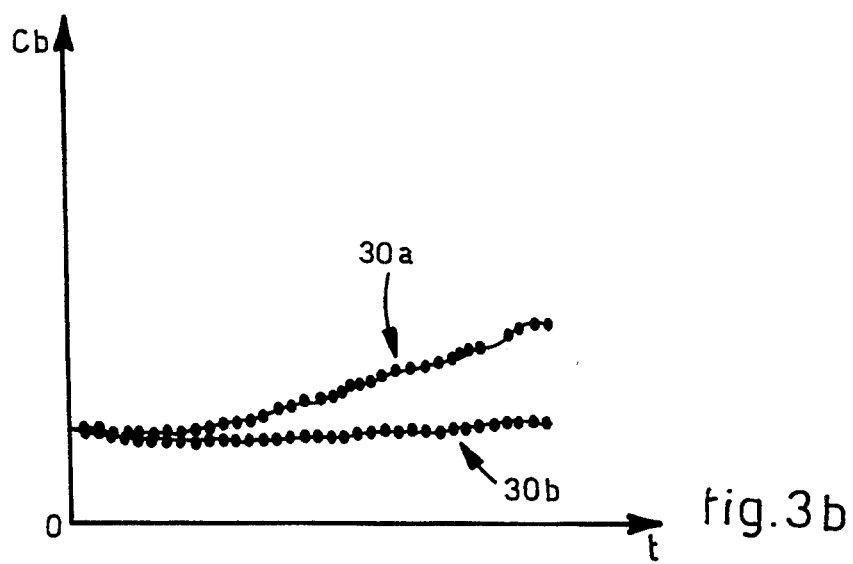

FIGS. 3a and 3b show two examples of growth curves produced with the apparatus according to the invention; the ordinate shows the parameter $C_B$, of formula $C_B = Ae^K n(t-t_o) + C$, relating to the bacterial concentration, while the abscissa shows the time in hours.

These curves are produced by interpolation of the points which the data processing unit 13 records as a function of the signal monitored with regular timing by the monitoring device 24.

To be more exact, FIG. 3a refers to the bacterial species of the Enterobacteriaceae, whereas FIG. 3b refers to the species of the yeasts.

Each of FIGS. 3a and 3b includes two curves, 30a and 30b respectively, relating to two different monitoring angles at which the monitors 28 are positioned.

The data processing unit 13 calculates the characteristic parameters of these curves 30a and 30b, that are (from formula $C_B = Ae^K n(t-t_o) + C$) A, C, $K_n$, etc.

Thereafter the data processing unit 13 compares these parameters with the values in its data bank, these values being characteristic for each particular bacterial species.

The results are given to the user by the data processing unit 13 by means of the display 14 or printer 16.

The inclusion of several monitors 28 at different angles makes it possible, in particular, to determine the form and size of the bacterial species present by evaluating the anisotropy of the signal monitored and by providing, therefore, more information about the type of bacterial colony within the sample.

By means of the keyboard 15 it is possible to set, at the start of the analysis cycle, all the parameters needed by the data processing unit 13 to perform its tasks, for instance by setting the number of samples present at the beginning on the stand 12, the samples added thereafter, the required analysis time, the procedure for displaying the results, etc.

I claim:

1. Apparatus for microbiological analysis of biological samples in liquid suspension by light-scattering technique, said apparatus comprising:

a plurality of test tube containers (11) made of a material transparent to electromagnetic radiations of a determined wave length;

a stand (12) with seatings (111) for positioning said containers (11) with a substantially vertical axis and including a thermostat system (17) for maintaining said containers within a predetermined temperature range, a stirring assembly (31) that includes keeper means (18) located within each container (11) for agitating the contents of each container, a reading means (26), which comprises a focussing and collimation system (22) having an axis of emission (29) substantially orthogonal to the vertical axis of the container (11) and also a monitoring device (24) for providing an output related to the radiation scattering of the contents of each container, a programmable means (13) for recording the output in radiation scattering of each container over time, for computing a curve fitting the recorded output for each container, for comparing each computed curve with stored curves of containers with known concentrations of known microbes, and for providing an indication of the concentration and microbe as an output, wherein said reading means (26) and the individual containers (11) are movable relative to each other, and said monitoring device (24) comprises at least one monitor (28) which, at least for a period of time during the analysis, is positioned on a plane substantially orthogonal to the vertical axis of one of said containers (11) and containing the axis (29) of emission and said one of said containers is also positioned at least at a fixed angle between 0° and 180° C. in relation to the axis (29) of emission.

2. Apparatus as in claim 1, wherein said at least one monitor comprises at least two monitors and the monitors are mounted for movement to-and-fro along the whole range of angles between 0° and 180° and are positioned stationary for a period of time with respect to said containers.

3. Apparatus as in claim 1, wherein said at least one monitor comprises at least two monitors and the monitors consist of a continuous band of monitors covering at least partly the angle between 0° and 180°.

4. Apparatus as in claim 1, in which the containers (11) are stationary and the reading means (26) has a temporary reading position for each container (11).

5. Apparatus as in claim 1, in which the containers (11) are movable and the reading means (26) is stationary, and each container (11) at least includes a position of cooperation with the reading means (26).

6. Apparatus as in claim 1, in which the focussing and collimation system (22) includes a generator (21) of electromagnetic radiation.

7. Apparatus as in claim 1, in which each container (11) is associated with a stirring assembly (31).

8. Apparatus as claim 1, in which the stirring assembly (31) is associated with the container (11) at least when said container is in cooperation with the reading means (26).

9. Apparatus as in claim 1, in which the programmable means (13) includes active and passive means for interacting with an operator of the unit.

10. Apparatus as in claim 1, in which the programmable means (13) governs all the functions of the apparatus.

* * * * *

UNITED STATES PATENT AND TRADEMARK OFFICE
CERTIFICATE OF CORRECTION

PATENT NO. : 5,356,815
DATED : October 18, 1994
INVENTOR(S) : Alfredo CIOTTI

It is certified that error appears in the above-indentified patent and that said Letters Patent is hereby corrected as shown below:

On the title page item [73], should read

--S.I.R.E. Sas di De Monte R., Duic G.B. & C.--.

Signed and Sealed this

Twenty-seventh Day of June, 1995

Attest:

BRUCE LEHMAN

Attesting Officer — Commissioner of Patents and Trademarks